(12) United States Patent
Kim et al.

(10) Patent No.: US 7,737,245 B2
(45) Date of Patent: Jun. 15, 2010

(54) PROCESS FOR PREPARING PHENOLIC POLYMER BY USING PHENOTHIAZINES MEDIATOR

(75) Inventors: Yong Hwan Kim, Daejeon (KR); Eun Suk An, Daejeon (KR); Keehoon Won, Daejeon (KR); Jae Kwang Song, Daejeon (KR); Jeong Yong Ryu, Daejeon (KR); Bong Keun Song, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 10/581,766

(22) PCT Filed: May 11, 2004

(86) PCT No.: PCT/KR2004/001086

§ 371 (c)(1),
(2), (4) Date: Jun. 6, 2006

(87) PCT Pub. No.: WO2005/054332

PCT Pub. Date: Jun. 16, 2005

(65) Prior Publication Data

US 2007/0260027 A1    Nov. 8, 2007

(30) Foreign Application Priority Data

Dec. 6, 2003    (KR)    ........................ 10-2003-0088349

(51) Int. Cl.
C08G 65/38    (2006.01)
C08G 61/02    (2006.01)

(52) U.S. Cl. ........................ 528/216; 528/86

(58) Field of Classification Search ............ 528/86, 528/216

See application file for complete search history.

(56) References Cited

U.S. PATENT DOCUMENTS

| 4,758,639 A | * | 7/1988 | Koyanagi et al. | ............ 526/62 |
| 4,900,671 A | | 2/1990 | Pokora et al. | |
| 4,913,697 A | * | 4/1990 | Saito et al. | ................. 528/205 |
| 5,153,298 A | * | 10/1992 | Pokora et al. | ................ 528/86 |
| 5,322,960 A | | 6/1994 | Sakamoto et al. | |

(Continued)

FOREIGN PATENT DOCUMENTS

JP    11-269254    10/1999

(Continued)

*Primary Examiner*—Mark Eashoo
*Assistant Examiner*—Liam J Heincer
(74) *Attorney, Agent, or Firm*—Frommer Lawrence & Haug LLP; Ronald R. Santucci

(57) ABSTRACT

The present invention relates to a process for preparing a phenolic polymer using a phenothiazine-based mediator, in particular, to a process for preparing a phenolic polymer via polymerization of phenolic monomers by using a phenothiazine-based mediator in the presence of peroxidase biocatalyst and an oxidant, thereby drastically improving the enzyme reactivity of peroxidase. The phenolic polymers prepared according to the polymerization of this invention maintain unsaturated hydrocarbon groups linked to their side chains, so that they are very useful as a curing resin because they can easily form coatings through radical curing. In addition, the coating formed using the curing resin has an antioxidation effect and a low surface energy, so that they can prevent physical attachment of marine livings. Because the antifouling-causing functional groups are not consumed, the coatings continuously exhibit durability.

10 Claims, 2 Drawing Sheets

U.S. PATENT DOCUMENTS

| | | | | |
|---|---|---|---|---|
| 5,407,972 A | * | 4/1995 | Smith et al. | 522/96 |
| 5,508,180 A | * | 4/1996 | Johnson et al. | 435/128 |
| 5,541,091 A | * | 7/1996 | Wheeler et al. | 435/128 |
| 5,637,387 A | * | 6/1997 | Chin et al. | 442/149 |
| 5,824,414 A | | 10/1998 | Kobayashi et al. | |
| 5,948,661 A | * | 9/1999 | Sjøholm | 435/192 |
| 5,968,883 A | * | 10/1999 | Cherry et al. | 510/305 |
| 6,150,491 A | * | 11/2000 | Akkara | 528/86 |
| 6,306,923 B1 | * | 10/2001 | Thepot et al. | 522/107 |
| 6,326,315 B1 | | 12/2001 | Uchiyama et al. | |
| 6,344,516 B1 | * | 2/2002 | Ikeda et al. | 524/717 |
| 6,962,965 B2 | * | 11/2005 | Yeager | 528/205 |
| 7,169,844 B2 | * | 1/2007 | Inokami | 524/591 |
| 2002/0119136 A1 | * | 8/2002 | Johansen | 424/94.4 |
| 2003/0229196 A1 | * | 12/2003 | Braat et al. | 528/86 |

FOREIGN PATENT DOCUMENTS

| | | |
|---|---|---|
| JP | 11323258 A * | 11/1999 |
| JP | 2002-201245 | 7/2002 |

* cited by examiner

PROCESS FOR PREPARING PHENOLIC POLYMER BY USING PHENOTHIAZINES MEDIATOR

This is a 371 filing of International Patent Application No. PCT/KR2004/001086 filed May 11, 2004 and published on Jun. 16, 2005 under publication number WO 2005/054332 A and claims priority benefits from South Korean Patent Application No. KR 10-2003-0088349 filed Dec. 6, 2003.

BACKGROUND OF THE INVENTION

1. Field of the Invention

The present invention relates to a process for preparing a phenolic polymer using a phenothiazine-based mediator, in particular, to a process for preparing a phenolic polymer by polymerizing phenolic monomers by use of a phenothiazine-based mediator in the presence of a peroxidase biocatalyst and an oxidant, thereby dramatically improving the enzyme reactivity of the peroxidase.

The phenolic polymers prepared according to the polymerization of this invention maintain unsaturated hydrocarbon groups linked to their side chains, so that they are very useful as a curing resin because they can easily form coatings through radical curing. In addition, the coatings formed using the curing resin have antioxidative effect and lower surface energy, so that they can prevent physical attachment of marine living beings. Because the antifouling-causing functional groups are not consumed, the coatings exhibit continuous durability.

2. Description of the Related Art

Phenolic polymers are known to be useful as paints and various coating materials, due to their excellent anti-corrosiveness and capability of forming a firm coating.

For synthesizing phenolic polymers chemically, formalin or hexamethylene tetraamine generated by the condensation of formaldehyde and ammonia is employed in high-temperature polymerization. However, this method some shortcomings in that formalin and formaldehyde are toxic and unreacted reactants toxic to environment and human body remain after the reaction. In addition, when phenolic polymers are synthesized using chemicals such as formalin, the double bonds of a lipid group side chain linked to the phenolic polymers are consumed, so that the resulting phenolic polymers is unlikely to form a coating due to the difficulty in setting by radical reaction.

Therefore, a biochemical preparation using a biocatalyst is recognized as a preferred environment-friendly approach instead of chemical synthesis using toxic materials.

Where phenolic polymers are synthesized using a biocatalyst such as an enzyme, it is essential to establish optimal polymerization conditions in consideration of substrate specificity of the enzyme. For example, a polymer derived from 4-methoxybenzyl alcohol and 2-hydroxy-4-methoxyphenyl acetic acid may not be synthesized using unassisted lignin peroxidase. In contrast, the presence of a mediator such as veratryl alcohol allows the polymerization to be promoted (Harvey et al., FEBS Lett. 195:242-246 (1986)). Furthermore, it has been known that phenolic compounds having significantly long alkyl chains at their meta-position cannot be polymerized by use of horseradish peroxidase. As discussed above, the polymerization of phenol compounds using a biocatalyst demands the establishment of optimal polymerization conditions because of substrate specificity of the enzyme.

The present inventors have conducted extensive research to develop a novel polymerization system which is applicable to all peroxidase biocatalysts generally known to be involved in the polymerization of phenolic monomers, and as a result, it has been found that phenothiazine derivatives could serve as mediators to activate enzymatic reaction of general peroxidases.

Accordingly, it is an object of this invention to provide a process for preparing a phenolic polymer by using a phenothiazine derivative as a mediator in a polymerization system of phenolic monomers using a general peroxidase biocatalyst.

Further, it is another object of this invention to provide use of the obtained phenolic polymers for preparing radical-curing resin.

Still further, it is another object of this invention to provide a coating material comprising the curing resin.

DETAILED DESCRIPTION OF THIS INVENTION

In one aspect of this invention, there is provided a process for preparing a phenolic polymer, which comprises polymerizing phenolic monomers with unsaturated aliphatic chains in the presence of a peroxidase biocatalyst and an oxidant; wherein said polymerizing phenolic monomers employs as a mediator a phenothiazine derivative substituted with an alkyl group or alkyl carbonic acid.

The present invention is described in more detail as follows.

The present invention improves the polymerization of phenolic monomers using peroxidase biocatalyst by adding phenothiazine-based mediators. This invention allows the increase of the overall yield and the polymerization of phenolic monomers at its meta-position substituted with long alkyl chains, which have been known not to polymerize in a peroxidase-catalyzed enzymatic reaction. In addition, the phenolic polymers generated by this invention maintain the double bonds of a lipid group linked to their side chain, so that they can easily form coatings through radical curing.

The striking feature of this invention lies in the addition of a specific mediator for the polymerization of phenolic monomers using a biocatalyst. The addition of the mediator greatly affects the reactivity of polymerization of phenolic monomers and the phenothiazine derivatives as mediators make the polymerization of phenolic monomers highly active. The phenothiazine derivatives serving as mediators in this invention are phenothiazine-based compounds substituted with an alkyl group or alkyl carbonic acid. More particularly, the exemplified phenothiazine derivatives are phenothiazine-based compounds substituted with an alkyl group having 1-6 carbon atoms or alkyl carbonic acid having 1-6 of carbon atoms. Further, the exemplified phenothiazine derivatives include ethylphenothiazine and phenothiazine-10-propionic acid.

The phenothiazine derivative is used in a concentration of 20-100 µM with respect to the total polymerization reactants. If the concentration of phenothiazine derivatives is lower than 20 µM, the effect derived from the addition of phenothiazine derivatives becomes far poorer; however, if the concentration is higher than 100 µM, the increase of concentration barely affects the polymerization. In addition, the excess of phenothiazine derivatives is very likely to induce the decrease of enzyme activity. Therefore, an excessive amount of phenothiazine derivatives is not suitable.

The phenolic monomers to be polymerized are aromatic hydrocarbons having unsaturated aliphatic substituents and hydroxyl groups, including natural-occurring and synthetic compounds. Plant-derived phenolic oils are preferable.

Exemplified phenolic monomers include cardanol, cardol, 2-methylcardol, urushiol, thitsiol, ranghol, laccol, 1-hydroxy-2-carboxy-3-pentanylbenzene, 1-hydroxy-2-carboxy-3-(8',11',11'-pentanylcadiyl)benzene, anacardic acid and zincoic acid. The plant-derived phenolic oils as raw materials in this invention are annually produced as by-product in the amount of about one million tons in the course of food production and the majority is consumed as a fuel. Therefore, the supply of phenolic oils is never problematic.

The present invention uses peroxidase as a biocatalyst and the scope of peroxidase type is broadened in this invention due to the use of phenothiazine mediator. The present invention may use any conventional peroxidase known to one skilled in the art. It is preferable that peroxidases derived from plants or fungi are used. More preferably, horseradish peroxidase, soybean peroxidase, Coprinus peroxidase or Aspergillus peroxidase are used. Preferably, peroxidase as a biocatalyst is used in the amount of 0.1-1.0 wt % with respect to the amount of the phenolic monomer. If the amount is less than 0.1 wt %, the reaction rate is greatly reduced thus requiring more time for polymerization; in contrast, if the amount is more than 1.0 wt %, the cost is increased and also the final polymers produced are obtained in a crosslinked form, and thus not applicable to paints or coatings.

It is generally known that oxidants are used in the polymerization of phenolic monomers using peroxidase. The present invention uses an oxidant known to one skilled in the art. As oxidants, hydrogen peroxide or organic hydrogen peroxide may be employed. The organic hydrogen peroxide includes hydroalkyl peroxide, in particular, t-butylhydroperoxide and ethylhydroperoxide. It is preferred that the amount of oxidant 0.1-1.0 mol with respect to 1 mol of the phenolic monomer. If the amount of oxidant is less than 0.1 mol, the yield of polymerization is decreased; in contrast, if the amount is more than 1.0 mol, the activity of peroxidase is remarkably reduced.

If necessary, an organic solvent is employed in the polymerization of phenolic monomers. It is recommended that the type of the organic solvent be selected depending on the type of phenolic monomers to be polymerized through experiments in view of stable maintenance of enzyme activity. It has been revealed that an alcoholic solvent such as isopropanol, methanol, ethanol and t-butanol is suitable in the polymerization of this invention. Other solvents have been revealed to greatly reduce the activity and stability of peroxidase as biocatalysts, resulting in a significant decrease in the yield of a polymer produced thereof. It is preferred that the organic solvent is used in the amount of 30-70 vol % with respect to the total polymerization volume. If the amount of organic solvent is less than 30 vol %, the solubility of phenolic monomers is decreased thus causing separation of layers in the reaction system, so that the high concentration of monomers may not be involved in the reaction. If the amount is more than 70 vol %, the activity of peroxidase as biocatalyst is drastically reduced and therefore the reaction is very unlikely to be maintained.

Further, it is important to adjust the pH range of a polymerization solution to promote the enzyme activity of peroxidase as biocatalysts. The pH range of the polymerization solution should be adjusted to fall within pH 5-8 by using a buffer.

The phenolic polymers produced under conditions described above maintain the double bonds of a lipid group linked to their side chains, so that they can easily form coatings through radical curing. In addition, the formed coatings have an antioxidative effect and their significantly low surface energy exhibit an antifouling effect thus preventing physical attachment of marine living beings similar to silicone-based antifouling coatings. Accordingly, in another aspect of this invention, there is provided the use of phenolic polymer obtained by the polymerization described above for preparing a radical cured resin.

In still another aspect of this invention, there is provided a coating comprising the radical cured resin.

The radical polymerization for preparing coatings of this invention may be controlled using transition metals and a complex of organic ligand serving as radical initiators. The transition metal and radical initiator applied to the curing are conventional ingredients used in the art to which the invention pertains.

The following examples are intended to be illustrative of this invention and should not be construed as limiting the scope of this invention as defined by the appended claims.

EXAMPLE

Cardanol (Palmer International, USA) isolated from Cashewnut extract was used as a phenolic monomer. Its purity was 90-95 wt % and contained about 3-6 wt % of cardol.

0.6 g of cardanol was dissolved in a mixed solution of 12.5 ml of isopropanol and 12.5 ml of a phosphate buffer (0.1 M, pH 7.0), and then 20 mg of horseradish peroxidase (Sigma, USA) were added to the resulting solution. Phenothiazine-10-propionic acid was added to the above mixture as a mediator to a concentration of 20-150 μM. Then, 300 μl of 30% hydrogen peroxide was homogenously added to the resultant mixture over a period of 6 hr. The reaction temperature was set at room temperature and the reaction solution was homogeneously mixed. Upon completion of the reaction, the reaction solution was concentrated under vacuum to remove isopropanol and then 20 ml of ethyl acetate was added. Thereafter, a solution layer dissolved in ethyl acetate solvent was collected after separation and concentrated under vacuum by removing the solvent. The activity of peroxidase involved in the reaction was measured according to the calorimetric method using ABTS (azinobisethylbenzothiazoline sulfonate). The molecular weight of the obtained product was measured using GPC (Gas permeation chromatography) equipped with a detector for refractive index. The mean molecular weight (Mw) of the obtained product was 8,000-12,000 g/mol and the average yield was above 60%.

Table 1 shows the change in yield of the phenolic polymer according to the concentration of phenothiazine-10-propionic acid as a mediator.

TABLE 1

Change in yield according to the concentration of phenothiazine-10-propionic acid

| Conc. (μM) | Yield (%) | Mean molecular weight ($M_w$) (Measurement with GPC) |
|---|---|---|
| 0 | 0 | — |
| 30 | 55 | 6,560 |
| 74 | 65 | 7,090 |
| 110 | 54 | 6,640 |
| 150 | 45 | 6,800 |

As indicated in Table 1, the reaction catalyzed by a peroxidase biocatalyst in the absence of a mediator did not lead to the polymerization of cardanol.

In addition, Table 2 represents the change in yield of the phenolic polymer according to the type of peroxidase.

TABLE 2

Yield change depending on the type of peroxidase

| Biocatalyst | | | |
|---|---|---|---|
| Type | Conc. (μM) | Yield (%) | Mean molecular weight ($M_w$) (Measurement with GPC) |
| HRP | 20 | 55 | 6,560 |
| SBP | 20 | 65 | 10,000 |
| CiP | 20 | 85 | 12,050 |
| AGP | 20 | 75 | 11,500 |

Note:
HRP (horseradish peroxidase), SBP (Soybean peroxidase) CiP (*Coprinus* peroxidase), AGP (*Aspergillus* peroxidase)

As indicated in Table 2, the presence of a phenothiazine-based mediator results in a greatly increased yield irrespective of the type of peroxidases.

Figure 1:
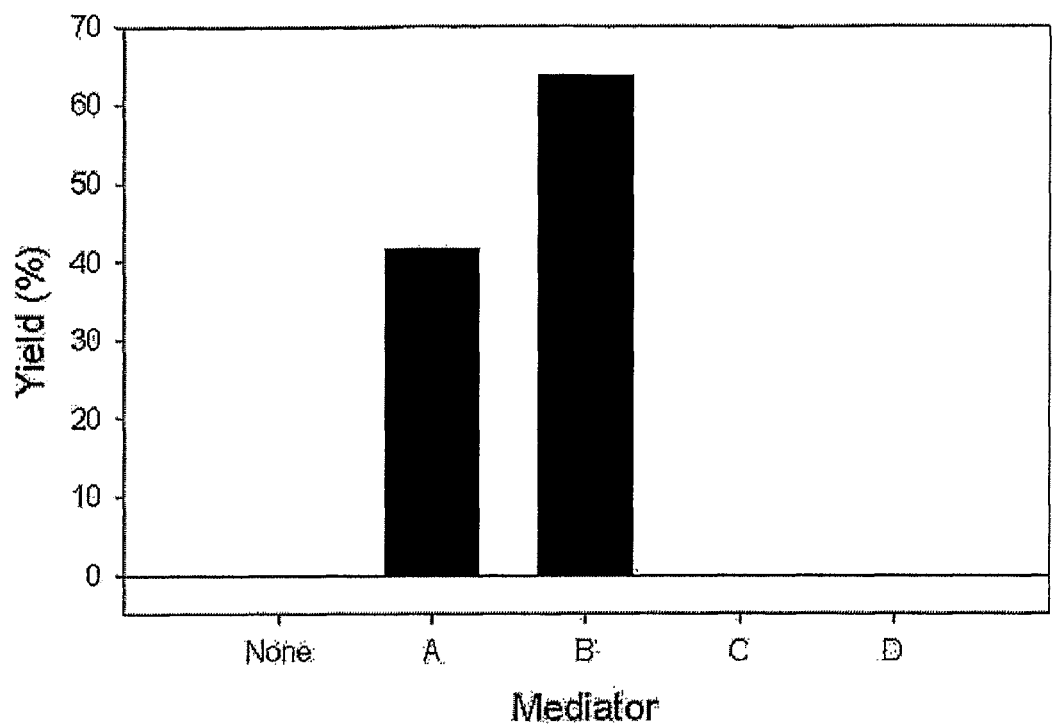
FIG. 1 is a graph representing the change in the polymerization yield of cardanol depending on the type of a mediator. (A: ethylphenothiazine, B: phenothizine-10-propionic acid, C: phenothiazine, and D: veratryl alcohol)

To examine the polymerization efficiency depending on the type of a mediator, the change of yield was analyzed under conditions described above with varying types of the mediators. The yield of phenolic polymer was examined using 74 μM of each of ethylphenothiazine(A), phenothiazine-10-propionic acid(B), phenothiazine(C) and veratryl alcohol(D) or no addition of a mediator. The results are summarized in Table 3 and FIG. 1, respectively.

TABLE 3

Yield change depending on the type of mediator

| Mediator | Yield (%) |
|---|---|
| No addition | 0 |
| Ethylphenothiazine | 42 |
| Phenothiazine-10-propionic acid | 65 |
| Phenothiazine | 0 |
| Veratryl alcohol | 0 |

Figure 2:
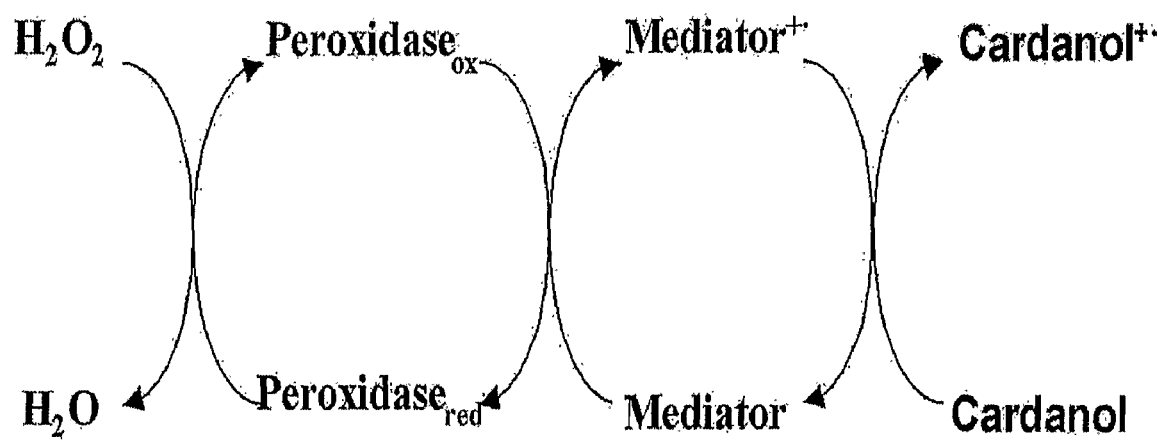
FIG. 2 represents the function of a mediator in the polymerization of cardanol.

The polymerization reactions using phenothiazine derivatives exhibited a considerable amount of yield. In particular, phenothiazine-10-propionic acid contributed to a remarkably high yield. This result suggests that propionic acid linked to phenothiazine increases the water-solubility of a mediator thus better facilitating its contact to horseradish peroxidase. As shown in FIG. 2, the mediator transfers electrons between horseradish peroxidase and cardanol substrate. Furthermore, phenothiazines not substituted with an alkyl group or alkyl carbonic acid did not help to promote the polymerization reaction. Ethylphenothiazine with an ethyl group in excess (2,000 μM) was revealed to mediate the polymerization of cardanol.

Figure 3:
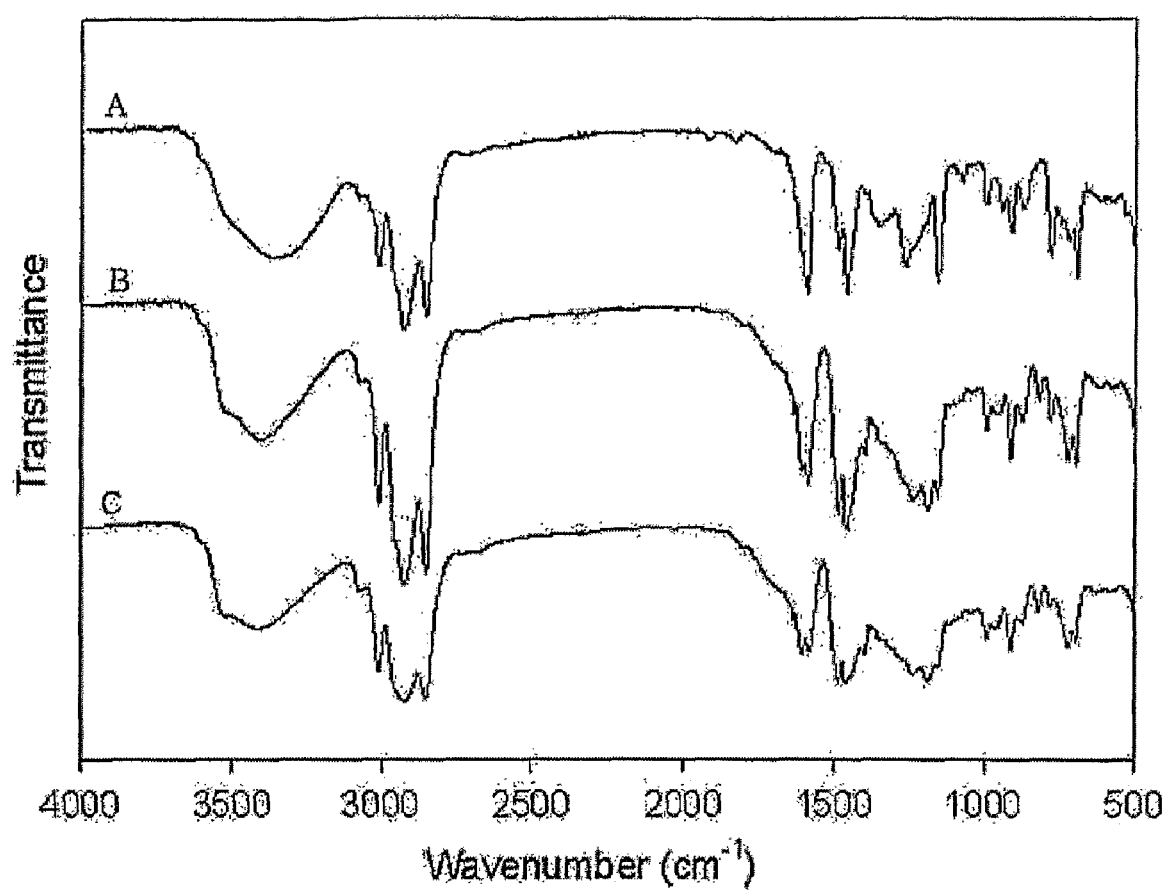
FIG. 3 represents the results of infrared spectrophotometry of cardanol polymer. (A: cardanol monomer, B: polycardanol (ethylphenothiazine), and C: polycardanol (phenothizine-10-propionic acid)).

In addition, as shown in FIG. 3, it was confirmed that the double bonds of a lipid group linked to the meta-position of cardanol are maintained intact with the addition of phenothiazine-10-propionic acid mediator, which was observed at 3050 $cm^{-1}$ on an infrared spectrophotometer. This result urges us to reason that the mediator may oxidize phenolic monomers in position-selective manner through intimate interaction with the enzyme. In other words, the double bond at 3050 $cm^{-1}$ was commonly observed in polycardanol generated by polymerization using cardanol monomers and a mediator.

Experimental Example 1

Evaluation on Antioxidation of Cured Coatings

The cured coatings were obtained by curing a phenolic polymer wherein cobalt naphthenate and methylethyl ketoperoxide were added to phenolic polymer prepared in the Example such as polycardanol, polycardol, polycardanol/phenol and polycardanol/ethylphenol.

1 ml of 500 pM 1,1-diphenyl-2-picryl hydrazine (DPPH) was added to 100 ml of distilled water and 1 g of coating was immersed in the resulting solution. The optical density of DPPH at 517 nm was measured with the lapse of time, which reflects the capacity of antioxidation. The results are summarized in Table 4.

TABLE 4

| Phenolic polymer | Antioxidation |
|---|---|
| Polycardanol | 60 |
| Polycardol | 70 |
| Polycardanol/phenol copolymer | 50 |
| Polycardanol/ethylphenol copolymer | 40 |
| Commercial-available phenolic resin (Novolak resin, Kukdochemical, Inc.) | 5 |

As indicated in Table 4, the phenolic polymer of this invention shows a better antioxidation result than conventional ones. The improved antioxidizing ability may prevent curing of an adhesive protein secreted by marine periphytons and therefore rendering it with an antifouling capacity.

Experimental Example 2

Evaluation on Antifouling Capacity of Cured Coatings

For evaluation on the antifouling capacity of each coating prepared in Experimental Example 1, the coating was immersed in sea water and the contamination by marine periphytons such as barnacles was examined. The results are summarized in Table 5.

TABLE 5

| Phenolic polymer | Antifouling capacity (No. of barnacles attached) |
|---|---|
| Polycardanol | 6 |
| Polycardol | 1 |
| Polycardanol/phenol copolymer | 12 |

TABLE 5-continued

| Phenolic polymer | Antifouling capacity (No. of barnacles attached) |
| --- | --- |
| Polycardanol/ethylphenol copolymer | 14 |
| Commercially available phenolic resin (Novolak resin, Kukdochemical, Inc.) | 35 |

As represented in Table 5, the attachment capacity of barnacles is significantly decreased by the cured coatings of phenolic polymer according to this invention. These results correspond to the antioxidation capacity indicated in Table 4.

INDUSTRIAL APPLICABILITY

As described previously, the most prominent feature of the present polymerization lies in the additional employment of phenothiazine-based mediators in polymerization of phenolic monomers using a peroxidase biocatalyst and an oxidant. The phenothiazine-based mediators exhibited activities for all peroxidases generally known to one skilled in the art, thus making it possible that phenolic monomers, which have not been able to be polymerized due to their long alkyl chains at their meta-position, to be polymerized.

In addition, the phenolic polymers prepared according to the polymerization of this invention can maintain unsaturated hydrocarbon groups linked to their side chains, so that they are very useful as a curing resin because they can easily form coatings via radical curing.

Further, the coatings formed using the curing resin exhibit a relatively low surface energy, so that they can prevent the physical attachment of marine living beings and the coatings can exhibit continuous durability because the antifouling-causing functional groups are not consumed.

The invention claimed is:

1. A process for preparing a phenolic polymer via polymerization of phenolic monomers having unsaturated aliphatic chains in the presence of peroxidase biocatalyst and an oxidant, wherein said polymerization uses as a mediator a phenothiazine derivative substituted with an alkyl group or alkyl carbonic acid.

2. The process according to claim 1, wherein said phenothiazine derivative is used in a concentration of 20-100 μM with respect to the total reactant.

3. The process according to claim 2, wherein said phenothiazine derivative is ethyl phenothiazine or phenothiazine-10-propionic acid.

4. The process according to claim 3, wherein said phenolic monomer is a plant phenolic oil.

5. The process according to claim 4, wherein said peroxidase biocatalyst is a plant- or fungus-derived peroxidase selected from the group consisting of horseradish peroxidase, soybean peroxidase, *Coprinus* peroxidase and *Aspergillus* peroxidase.

6. The process according to claim 1, wherein said phenothiazine derivative is ethyl phenothiazine or phenothiazine-10-propionic acid.

7. The process according to claim 1, wherein said phenolic monomer is a plant phenolic oil.

8. The process according to claim 1, wherein said peroxidase biocatalyst is a plant- or fungus-derived peroxidase.

9. The process according to claim 8, wherein said peroxidase biocatalyst is a plant- or fungus-derived peroxidase selected from the group consisting of horseradish peroxidase, soybean peroxidase, *Coprinus* peroxidase and *Aspergillus* peroxidase.

10. The process according to claim 1, wherein said oxidant is hydrogen peroxide or hydroalkyl peroxide.

* * * * *